(12) United States Patent
Hwang et al.

(10) Patent No.: US 8,272,091 B2
(45) Date of Patent: Sep. 25, 2012

(54) ELECTRIC TOOTHBRUSH AND METHOD FOR CONTROLLING THEREOF

(75) Inventors: Jin Sang Hwang, Suwon-si (KR); Jeong-Whan Lee, Chungju-si (KR)

(73) Assignee: Xiu Solutions Co., Ltd., Gyeonggi-Do (KR)

( * ) Notice: Subject to any disclaimer, the term of this patent is extended or adjusted under 35 U.S.C. 154(b) by 538 days.

(21) Appl. No.: 12/519,033

(22) PCT Filed: Dec. 11, 2007

(86) PCT No.: PCT/KR2007/006421
§ 371 (c)(1),
(2), (4) Date: Jun. 12, 2009

(87) PCT Pub. No.: WO2008/072871
PCT Pub. Date: Jun. 19, 2008

(65) Prior Publication Data
US 2010/0106336 A1    Apr. 29, 2010

(30) Foreign Application Priority Data
Dec. 12, 2006    (KR) .................. 10-2006-0125968

(51) Int. Cl.
*A61C 17/22* (2006.01)
(52) U.S. Cl. ........................................ 15/22.1
(58) Field of Classification Search ............. 15/22.1
See application file for complete search history.

(56) References Cited

U.S. PATENT DOCUMENTS

| 4,149,291 | A | * | 4/1979 | Stoltz ........................ 15/22.1 |
| 4,544,816 | A | * | 10/1985 | Benz ......................... 200/52 R |
| 4,716,614 | A | | 1/1988 | Jones et al. |
| 5,561,881 | A | * | 10/1996 | Klinger et al. ............. 15/22.1 |
| 5,794,296 | A | * | 8/1998 | Wong ............................. 15/23 |
| 6,536,068 | B1 | | 3/2003 | Yang et al. |
| 6,850,167 | B2 | | 2/2005 | Rosen |
| 2007/0151051 | A1 | * | 7/2007 | Filsouf ....................... 15/22.1 |

FOREIGN PATENT DOCUMENTS

| DE | 40 12 413 A1 | | 10/1991 |
| FR | 2659848 | * | 9/1991 |
| JP | 2005-152217 | * | 6/2005 |

OTHER PUBLICATIONS

International Search Report (Form PCT/ISA/210) for International Application No. PCT/KR2007/006421, mailed Mar. 24, 2008.

* cited by examiner

*Primary Examiner* — Mark Spisich
(74) *Attorney, Agent, or Firm* — Staas & Halsey LLP (57) ABSTRACT

An electric toothbrush is disclosed. The electric toothbrush according to some example embodiments includes a bristle-vibrating unit that vibrates toothbrush bristles to clean a side of teeth in contact with the toothbrush bristles, a bristle direction-sensing unit detecting a direction to which the toothbrush bristles are directed in an oral cavity and a control unit automatically controlling the bristle-vibrating unit in response to the detected direction such that the vibration intensity of the toothbrush bristles when an occlusal side is brushed is weaker than the vibration intensity when a buccal side or a lingual side is brushed.

20 Claims, 11 Drawing Sheets

ELECTRIC TOOTHBRUSH AND METHOD FOR CONTROLLING THEREOF

CROSS REFERENCE TO RELATED PATENT APPLICATIONS

This application claims the benefit under 35 U.S.C. Section 371, of PCT International Application No. PCT/KR2007/006421, filed Dec. 11, 2007, which claimed priority to Korean Patent Application No. 10-2006-0125968, filed Dec. 12, 2006 in the Korean Intellectual Property Office, the disclosures of which are hereby incorporated by reference

TECHNICAL FIELD

Embodiments relate to an electric toothbrush and a method for controlling thereof. More particularly, embodiments relate to an electric toothbrush capable of automatically controlling a vibration intensity of the electric toothbrush according to a portion of teeth being brushed, and uniformly and efficiently brushing each portion of the teeth, and a method for controlling thereof.

BACKGROUND ART

Since human beings started cleaning teeth, or toothbrushing, with a toothbrush, a number of theories on proper toothbrushing habits have been continuously suggested and publicized by many persons, such as toothbrush manufacturers, dentists, etc.

Electric toothbrushes have been developed for the disabled, and are now widely used for convenience in busy lifestyles. An electric toothbrush vibrates by employing a motor, or by using sonic or ultrasonic waves such that plaque is removed in response to the vibration. Processes of removing the plaque are slightly different according to the number of vibrations per minute.

There is an opinion that the plaque is efficiently removed if the electric toothbrush vibrates more than 20,000 times per minute. Furthermore, there is an opinion that, if the electric toothbrush vibrates more than 30,000 times per minute, the plaque is more efficiently removed, but harmful side effects may occur. If the electric toothbrush vibrates at a high frequency (i.e., more than 20,000 times per minute), then toothbrush bristles in contact with a tooth may also remove the plaque on the opposite side of the tooth due to the vibration. That is, toothbrush manufacturers argue that, once the toothbrush bristles are in contact with the front side of the tooth, the plaque at the reverse side of the tooth can be removed.

Such an electric toothbrush may be relatively less affected by toothbrushing patterns, or the toothbrushing habits, of a user. The electric toothbrush, however, has a problem in that the electric toothbrush may not provide the user with feedback on whether the user has positioned the toothbrush bristles evenly on all portions of the teeth (so that the teeth are uniformly brushed). An intensity control mode of the electric toothbrush is implemented for the user to control the vibration intensity. The electric toothbrush having the intensity control mode, however, has another problem in that toothbrushing must be stopped to adjust the vibration intensity when the vibration intensity is controlled according to each portion of the teeth. If the user does not adjust the vibration intensity because the user finds that controlling the vibration intensity is troublesome, various gum diseases may occur.

In order to mitigate these problems, electric toothbrushes having various embedded functionalities have been suggested such that motivation is provided for the user to maintain the toothbrushing during a recommended time interval, which may be set to about 2 to 3 minutes.

As a related art relating to such electric toothbrushes, the Oral-B Triumph electric toothbrush released in 2006 displays an actual toothbrushing time in units of seconds on a liquid crystal display (LCD) display window embedded in the body unit of the electric toothbrush. Once the power of the electric toothbrush is turned on, the toothbrushing time is counted from the turn-on time, and the toothbrushing time is displayed on the display window. The electric toothbrush vibrates for a short time four times every 30 seconds for the user to brush four regions of the teeth during the whole recommended toothbrushing time of 2 minutes, and displays a completion mark on the display window after about 2 minutes has elapsed from the turn-on time. Functions of the electric toothbrush are disclosed such that the user can select a cleaning mode, a soft-cleaning mode, a massage mode or a whitening mode by controlling the number of vibrations per minute or the vibration method.

The Sonicare Elite e9000 series released by Philips includes electric toothbrushes of which vibrations are induced by sonic waves. The electric toothbrushes gradually increase the vibration intensity for the user, even if the user has not experienced brushing teeth with the electric toothbrush, so that the user can adapt to the intensity or speed of the vibration by automatically controlling the vibration intensity during the first 14 times. A function for manually controlling the speed is also disclosed such that the speed is controlled by a two-speed control function for a user having sensitive gums.

The RC-300UJ Ultima Ultrasonic Toothbrush released by Toray Ireeve Corp. vibrates 16,000 times per second using ultrasonic waves (of 1.6 MHz) transmitted from a portion of the toothbrush bristles.

The conventional art described above cannot inform the user as to which portion has been brushed since the conventional toothbrushes cannot identify locations of the toothbrushes. Accordingly, since the conventional toothbrushes cannot guide the user to properly clean each portion of the teeth, the conventional toothbrushes have problems in that motivation may not be provided for the user to maintain brushing of the teeth for the recommended toothbrushing time. Moreover, motivation may not be provided for the user to uniformly brush all portions of the teeth, and a habit correction may not be easily accomplished even though parents or another person tries to monitor the toothbrushing habits of the user.

There is a tendency for the user to weakly brush a labial side and both buccal sides of the teeth, and relatively strongly brush an occlusal side of the teeth. However, since products currently released cannot recognize the location of a toothbrush, or since the products cannot automatically control the vibration speed according to brushed portions of the teeth, the products have problems in that the user has to adjust the vibration intensity during the toothbrushing according to the location of the toothbrush. Accordingly, the conventional toothbrushes have a problem in that periodontitis or gingivitis may occur.

DISCLOSURE OF THE INVENTION

Technical Problem

Embodiments provide an electric toothbrush and a method for controlling an electric toothbrush capable of providing feedback of toothbrushing time according to a portion of teeth being brushed for a user to uniformly brush the teeth.

Embodiments provide an electric toothbrush and a method for controlling an electric toothbrush capable of automatically controlling vibration intensity to ease problems, such as gum recession, tooth abrasions, etc. caused by hard toothbrushing.

Technical Solution

According to one aspect, there is provided an electric toothbrush including a bristle-vibrating unit, a bristle direction-sensing unit and a control unit. The bristle-vibrating unit is configured to vibrate toothbrush bristles to clean a side of teeth in contact with the toothbrush bristles. The bristle direction-sensing unit is configured to detect a direction to which the toothbrush bristles are directed in an oral cavity, wherein the direction may be one of directions toward a buccal side, a lingual side and an occlusal side. The buccal side is the outer side of the teeth, the lingual side is the inner side of the teeth, and the occlusal side is a chewing side of the teeth. The control unit is configured to automatically control the bristle-vibrating unit in response to the detected direction such that the vibration intensity of the toothbrush bristles when the buccal side or the lingual side is brushed is weaker than the vibration intensity when the occlusal side is brushed.

In some embodiments, the bristle-vibrating unit may include a three-axis acceleration sensor, wherein an x-axis of the three-axis acceleration sensor may be directed along a direction that is perpendicular to a toothbrush handle length direction and to a toothbrush bristle direction, wherein a y-axis of the three-axis acceleration sensor may be directed along the toothbrush handle length direction, and wherein a z-axis of the three-axis acceleration sensor may be directed along the toothbrush bristle direction.

In other embodiments, the bristle-vibrating unit may include a pair of acceleration sensors, wherein axis directions of the acceleration sensors may be perpendicular to a y-axis directed along a toothbrush handle length direction, wherein the axis directions of the acceleration sensors may be inclined at a positive predetermined angle and a negative predetermined angle, respectively, with reference to an x-axis that is perpendicular to the toothbrush handle length direction and to a toothbrush bristle direction, and wherein the acceleration sensors may be arranged symmetrically to each other.

In some embodiments, the bristle direction-sensing unit may detect the direction to which the toothbrush bristles are directed by dividing the detected direction into a direction toward an upper occlusal side, a direction toward a lower occlusal side, a direction toward a left buccal side or a left lingual side, and a direction toward a right buccal side or a right lingual side.

In further embodiments, the electric toothbrush may further include a timer configured to count a toothbrushing time for the detected direction, and a feedback unit configured to provide a user with at least one of visual feedback, auditory feedback and tactile feedback when the counted toothbrushing time reaches a predetermined recommended toothbrushing time.

According to one aspect, there is provided a method of automatically controlling the vibration intensity of an electric toothbrush. In the method of automatically controlling the vibration intensity, a direction to which toothbrush bristles are directed is detected in an oral cavity by a bristle direction-sensing unit, wherein the direction may be one of directions toward a buccal side, a lingual side and an occlusal side. The buccal side is the outer side of teeth, the lingual side is an inner side of the teeth, and the occlusal side is a chewing side of the teeth. Thereafter, the vibration intensity of the toothbrush bristles is controlled in response to the detected direction such that the vibration intensity when the buccal side or the lingual side is brushed is weaker than the vibration intensity when the occlusal side is brushed.

In some embodiments, the direction to which the toothbrush bristles are directed may be detected by dividing the detected direction into a direction toward an upper occlusal side, a direction toward a lower occlusal side, a direction toward a left buccal side or a left lingual side, and a direction toward a right buccal side or a right lingual side.

In further embodiments, a toothbrushing time for the detected direction is counted, and a user is provided with at least one of visual feedback, auditory feedback and tactile feedback when the counted toothbrushing time reaches a predetermined recommended toothbrushing time.

According to one aspect, there is provided an electric toothbrush including a bristle-vibrating unit, a bristle direction-sensing unit, a timer, a feedback unit and a control unit. The bristle-vibrating unit is configured to vibrate toothbrush bristles to clean a side of teeth in contact with the toothbrush bristles. The bristle direction-sensing unit is configured to detect a direction to which the toothbrush bristles are directed in an oral cavity, wherein the direction may be one of directions toward a buccal side, a lingual side and an occlusal side. The buccal side is an outer side of the teeth, the lingual side is an inner side of the teeth, and the occlusal side is a chewing side of the teeth. The timer is configured to count a toothbrushing time for the detected direction. The feedback unit is configured to provide a user with at least one of visual feedback, auditory feedback and tactile feedback. The control unit is configured to control the bristle-vibrating unit, and is configured to control the feedback unit to provide the user with the at least one type of feedback when the counted toothbrushing time reaches a predetermined recommended toothbrushing time by checking the toothbrushing time provided from the timer in response to the detected direction.

In some embodiments, the control unit may be configured to control the feedback unit to provide the user with feedback about an insufficiency state if the toothbrushing time of any portion of the teeth is shorter than a predetermined recommended toothbrushing time by checking the toothbrushing time of each of a plurality of portions of the teeth in response to the detected direction.

Advantageous Effect

According to an aspect, the electric toothbrush with a sensing function for the location of the electric toothbrush may be manufactured at low cost so that the general public may use the electric toothbrush. Accordingly, the electric toothbrush may contribute to public health. Moreover, the electric toothbrush according to some embodiments of the present invention may provide feedback for the user to brush each portion of teeth during an appropriate time, thereby providing motivation for the user to uniformly brush the teeth.

Further, the electric toothbrush may automatically control the vibration intensity by detecting a portion of the teeth being brushed so that the user may brush the teeth comfortably since the electric toothbrush vibrates at an appropriate intensity for the user. Accordingly, the user may clean the teeth efficiently.

The electric toothbrush also may provide feedback of toothbrushing time according to the detected portion in real-time so that the user may easily evaluate his or her toothbrushing pattern.

Further, if children use the electric toothbrush, a guardian may check whether the children have brushed the teeth or whether the children have brushed with a proper toothbrushing pattern since whether toothbrushing is performed with the proper toothbrushing pattern depending on portions of the teeth is stored as a result value or a score.

BRIEF DESCRIPTION OF THE DRAWINGS

The above and other advantages of the embodiment will become more apparent by describing in detail example embodiments thereof with reference to the accompanying drawings, in which.

BEST MODE FOR CARRYING OUT THE INVENTION

Embodiments now will be described more fully with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Figure 1:
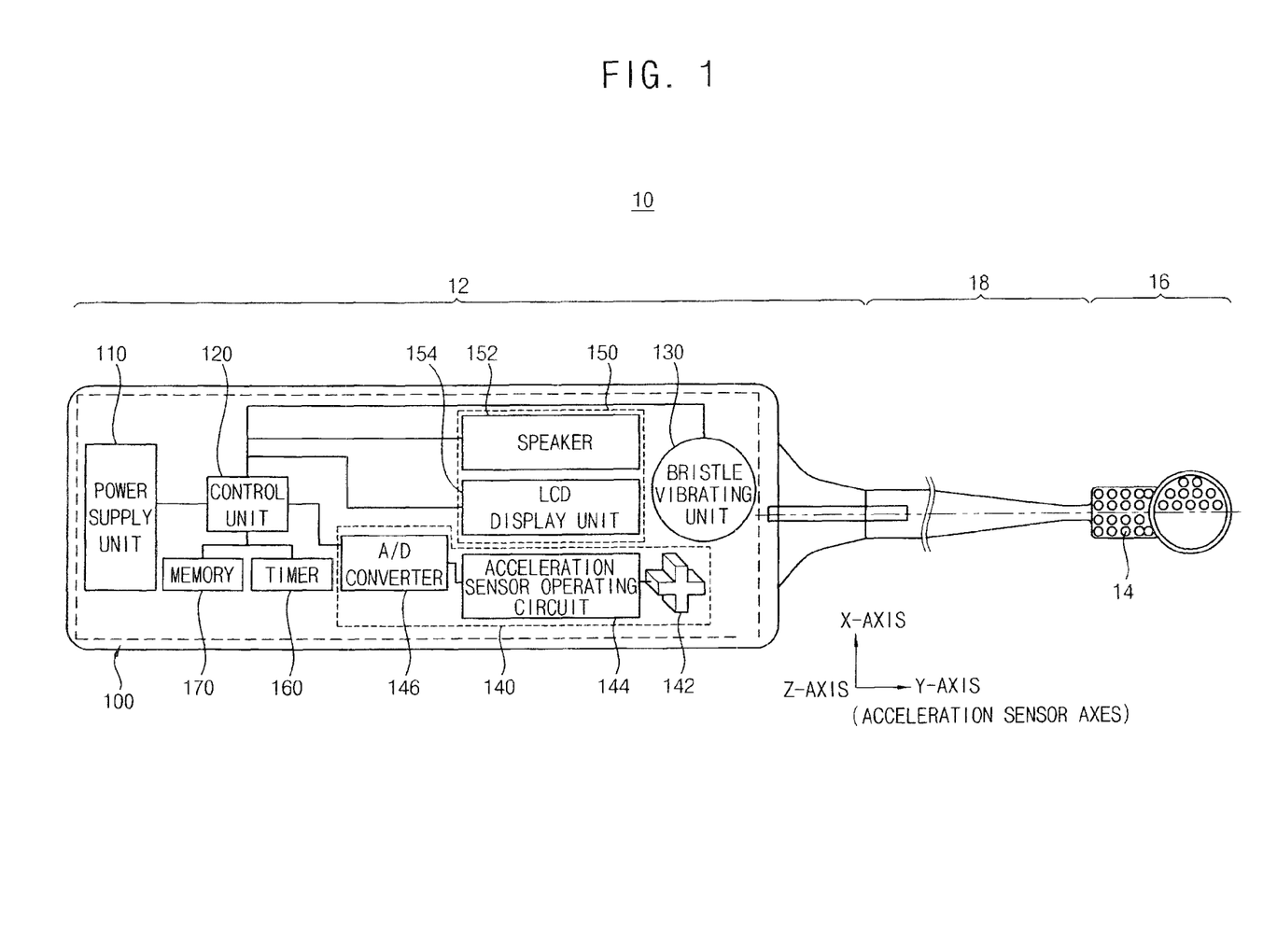
FIG. 1 is a diagram illustrating an electric toothbrush according to an example embodiment.

FIG. 1 is a diagram illustrating an electric toothbrush according to an example embodiment.

Referring to FIG. 1, an electric toothbrush 10 includes a toothbrush handle 12 (i.e., a toothbrush body 12), a toothbrush head 16 on which toothbrush bristles 14 are formed, and a toothbrush neck 18 that is integrally formed with the toothbrush head 16 and is detachably attached to the toothbrush body 12. An electrically powered unit 100 is embedded in the toothbrush body 12.

The electrically powered unit 100 includes a power supply unit 110, a control unit 120, a bristle-vibrating unit 130, a bristle direction-sensing unit 140, a feedback unit 150, a timer 160 and a memory 170.

The power supply unit 110 is a unit for providing an operating voltage required in each unit included in the electrically powered unit 100. The power supply unit 110 may be a power supply unit of a typical electric toothbrush, which includes a battery for charge, a charge/discharge control circuit, etc.

The control unit 120 may be implemented as a one-chip microprocessor or a microcomputer, which is configured to perform an electric toothbrush control program according to the embodiment. The control unit 120 controls the timer 160 to input toothbrushing time information, and then stores the inputted information or operation data in the memory 170.

The bristle-vibrating unit 130 may employ a typical vibration generator. In some embodiments, the bristle-vibrating unit 130 may alternatively employ a rotary motor such that the toothbrush bristles rotates in a direction. In other embodiments, the bristle-vibrating unit 130 may generate ultrasonic waves to vibrate the toothbrush bristles.

The feedback unit 150 may provide a user with visual feedback, auditory feedback, or tactile feedback. The feedback unit 150 may include a speaker 152 for the auditory feedback and a liquid crystal display (LCD) display unit 154 for the visual feedback. Further, the bristle-vibrating unit 130 may be used to provide the tactile feedback. For example, the bristle-vibrating unit 130 may generate vibration having a frequency that is different from a frequency of the vibration for toothbrushing so as to provide the user with the tactile feedback.

The bristle direction-sensing unit 140 includes a three-axis acceleration sensor 142, an acceleration sensor operating circuit 144 and an analog-to-digital converter 146 so as to detect a direction to which an end of the toothbrush bristles 14, formed on the toothbrush head 16, is directed. The three-axis acceleration sensor 142 is installed in the electrically powered unit 100 such that an x-axis is directed along a direction that is perpendicular to a toothbrush handle length direction and to a toothbrush bristle direction, a y-axis is directed along the toothbrush handle length direction, and a z-axis is directed along the toothbrush bristle direction. The acceleration sensor 142 may be a typical accelerometer for measuring acceleration, which includes a mass for detecting acceleration, a spring supporting the mass, a damper using silicon-based oil or the like, a displacement measuring element for secondarily converting a firstly transformed acceleration signal having a displacement form into a resultant electric signal. The accelerometer may be classified as a one-axis-type accelerometer, a two-axis-type accelerometer or a three-axis-type accelerometer according to the degree of freedom of detection directions. The accelerometer may also be classified as a strain gauge-type accelerometer, a piezoelectric accelerometer, a differential transformer-type accelerometer, a potentiometer-type accelerometer, a servo-type accelerometer, etc., according to a type of a displacement sensor for the secondary conversion. In one example embodiment, a three-axis acceleration sensor such as the MMA7260Q manufactured by Freescale Semiconductor, Inc. may be employed.

Figure 2:
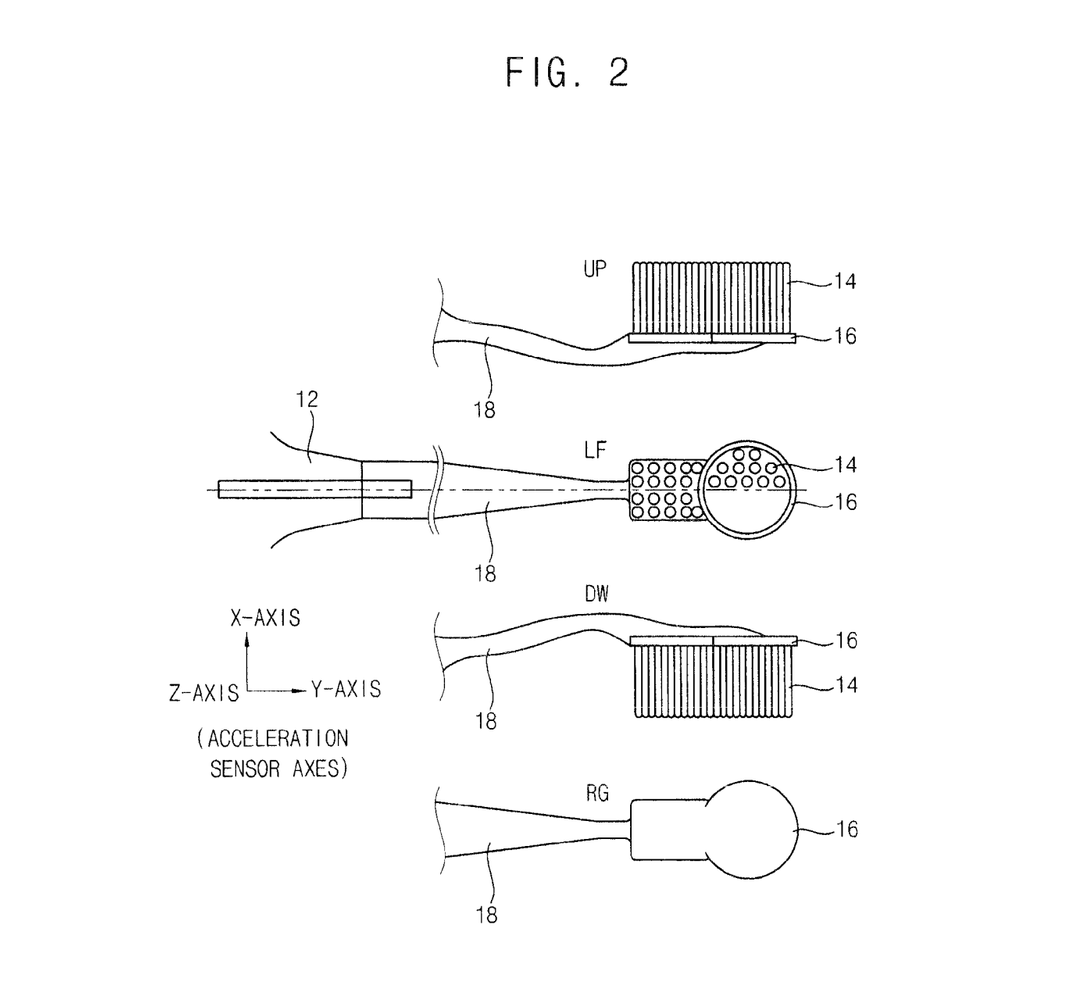
FIGS. 2 and 3 are diagrams for describing operations of a bristle direction-sensing unit according to an example embodiment.
Figure 3:
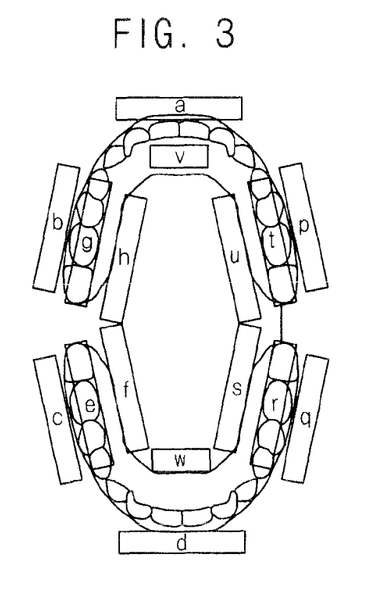
Figure 4:
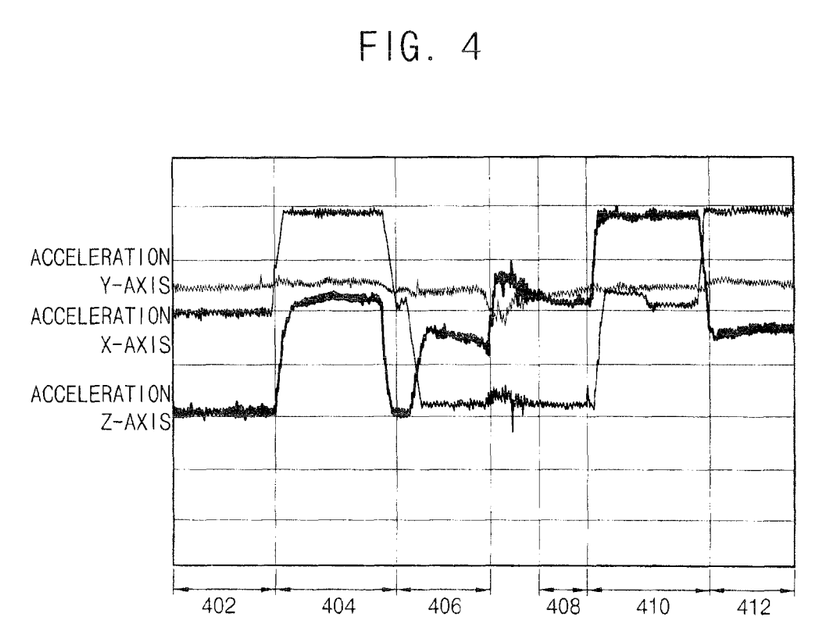
FIG. 4 is a wave diagram illustrating output signals of a bristle direction-sensing unit having a three-axis acceleration sensor.

Hereinafter, operations of the acceleration sensor 142 according to some example embodiments will be described with reference to FIGS. 1 through 4. FIG. 2 is a diagram for describing directions of toothbrush bristles, FIG. 3 is a diagram illustrating teeth divided into 16 portions in an oral cavity, and FIG. 4 is a wave diagram illustrating output signals of the acceleration sensor 142 according to each axis when 10 portions illustrated in FIG. 3 are brushed. The name of each portion is referred to as described in Table 1.

TABLE 1

| PORTION SYMBOL | PORTION NAME |
| --- | --- |
| a | upper front labial side |
| b | upper left buccal side |
| c | lower left buccal side |
| d | lower front labial side |
| e | lower left occlusal side |
| f | lower left lingual side |
| g | upper left occlusal side |
| h | upper left lingual side |
| p | upper right buccal side |
| q | lower right buccal side |
| r | lower right occlusal side |
| s | lower right lingual side |

TABLE 1-continued

| PORTION SYMBOL | PORTION NAME |
|---|---|
| t | upper right occlusal side |
| u | upper right lingual side |
| v | upper front lingual side |
| w | lower front lingual side |

The acceleration sensor 142 installed in the bristle direction-sensing unit 140 according to some example embodiments generates a detection signal for detecting bristle directions UP, RG, DW and LF illustrated in FIG. 2 by outputting direct currents that are different from one another according to the axes (i.e., the x-axis, the y-axis and the z-axis).

As described with reference to teeth portions, if the toothbrush bristles 14 are directed along an up direction UP illustrated in FIG. 2, then portions g and t of teeth (i.e., upper occlusal sides) illustrated in FIG. 3 are brushed. When the toothbrush bristles 14 are directed along a right direction RG, portions a, b, c and d of the teeth (i.e., labial and left buccal sides) are brushed. When the toothbrush bristles 14 are directed along a down direction DW, portions e and r of the teeth (i.e., lower occlusal sides) are brushed. When the toothbrush bristles 14 are directed along a left direction LF, portions p and q of the teeth (i.e., right buccal sides) are brushed. These portions related to directions of the toothbrush bristles 14 are described based on right-handedness. The toothbrush bristles 14 may be directed along the right direction RG while a person, who brushes his teeth with the right hand, brushes the front side and left side of the teeth. The right-handed person may generally turn the toothbrush around a toothbrush handle length direction by 180 degrees such that the toothbrush bristles 14 may be directed along the left direction LF for the right-handed person to brush the right side of the teeth with the right hand.

On this basis, detection results of directions to which the toothbrush bristles 14 are directed, which are produced by using the acceleration sensor 142, will be described with reference to the wave diagram of FIG. 4.

Referring to FIGS. 2 through 4, when a right-handed user brushes the portions a and d (i.e., the labial side of front teeth when the upper teeth and lower teeth are in contact) or the portions b and c (i.e., the buccal side of left molars when the upper teeth and lower teeth are in contact), output signals of the acceleration sensor 142 may be represented as first through third waves in a first period 402 since the toothbrush bristles 14 may be directed along the right direction RG. In this case, the level of the second wave related to the y-axis is larger than the level of the first wave related to the x-axis and the level of the first wave related to the x-axis is larger than the level of the third wave related to the z-axis.

When the right-handed user brushes the portion g (i.e., the occlusal side of upper left molars), output signals of the acceleration sensor 142 may be represented as the first through third waves in a second period 404 since the toothbrush bristles 14 may be directed along the up direction UP. In this case, the levels of the first through third waves related to x-axis, y-axis and z-axis, respectively, may be expressed as: x-axis>y-axis>z-axis.

When the right-handed user brushes the portion e (i.e., the occlusal side of lower left molars), output signals of the acceleration sensor 142 may be represented as the first through third waves in a third period 406 since the toothbrush bristles 14 may be directed along the down direction DW. In this case, the levels of the first through third waves related to x-axis, y-axis and z-axis, respectively, may be expressed as: y-axis>z-axis>x-axis.

When the right-handed user brushes the portion r (i.e., the occlusal side of lower right molars), output signals of the acceleration sensor 142 may be represented as the first through third waves in a fourth period 408 since the toothbrush bristles 14 may be directed along the down direction DW. In this case, the levels of the first through third waves related to x-axis, y-axis and z-axis, respectively, may be expressed as: x-axis>y-axis>z-axis.

When the right-handed user brushes the portions p and q (i.e., buccal side of right molars when upper teeth and lower teeth are in contact), output signals of the acceleration sensor 142 may be represented as the first through third waves in a fifth period 410 since the toothbrush bristles 14 may be directed along the left direction LF. In this case, the levels of the first through third waves related to x-axis, y-axis and z-axis, respectively, may be expressed as: z-axis>y-axis>x-axis.

When the right-handed user brushes the portion t (i.e., the occlusal side of upper right molars), output signals of the acceleration sensor 142 may be represented as the first through third waves in a sixth period 412 since the toothbrush bristles 14 may be directed along the up direction UP. In this case, the levels of the first through third waves related to x-axis, y-axis and z-axis, respectively, may be expressed as: x-axis>y-axis>z-axis.

As described above, the three-axis acceleration sensor outputs direct currents related to the x-axis, the y-axis and the z-axis, respectively, in response to a direction of a device where the three-axis acceleration sensor is installed, and thus a direction of the toothbrush bristles 14 may be detected by analyzing levels of the direct currents related to the axes. As described in FIG. 4, four directions of up, down, left and right directions may be estimated by analyzing the levels of the direct currents related to only the x-axis and the z-axis since the level of the direct current related to the y-axis hardly varies.

If a vibration speed is faster than a certain speed, the electric toothbrush in contact with the buccal side of teeth may also remove plaque on the lingual side of the tooth. Therefore, the user need only contact the electric toothbrush with the four portions of the teeth in order to brush every portion of the teeth.

Table 2 presented below illustrates relations between detected directions of the toothbrush bristles 14 and the portions of the teeth that may be estimated by using the detected directions.

TABLE 2

| | BRISTLE DIRECTION | | | |
| | RG | UP | DW | LF |
|---|---|---|---|---|
| SENSED PORTION | a, b, c, d | g, t | e, r | p, q |

As described in Table 2, four portions of the teeth to be brushed may be detected with the three-axis acceleration sensor, and thus effective feedback may be provided for the user based on the detected portions. The LCD display unit 154 illustrated in FIG. 1 may be installed in a back side of the electric toothbrush to provide visual feedback instructing the user to change the brushed portions, which is reflected on a mirror when the user brushes the teeth. For example, the LCD display unit 154 may display at least one of a time point when the preceding toothbrushing starts, an elapsed toothbrushing time and a score of a toothbrushing pattern. In some embodiments, the score may be calculated in a lookup table manner based on the toothbrushing time of the timer 160 and information on the detected directions of the toothbrush bristles, or otherwise may be calculated by performing an operation on the number of target satisfactory events representing actual toothbrushing time for each portion that satisfies a predetermined brushing time.

Figure 5:
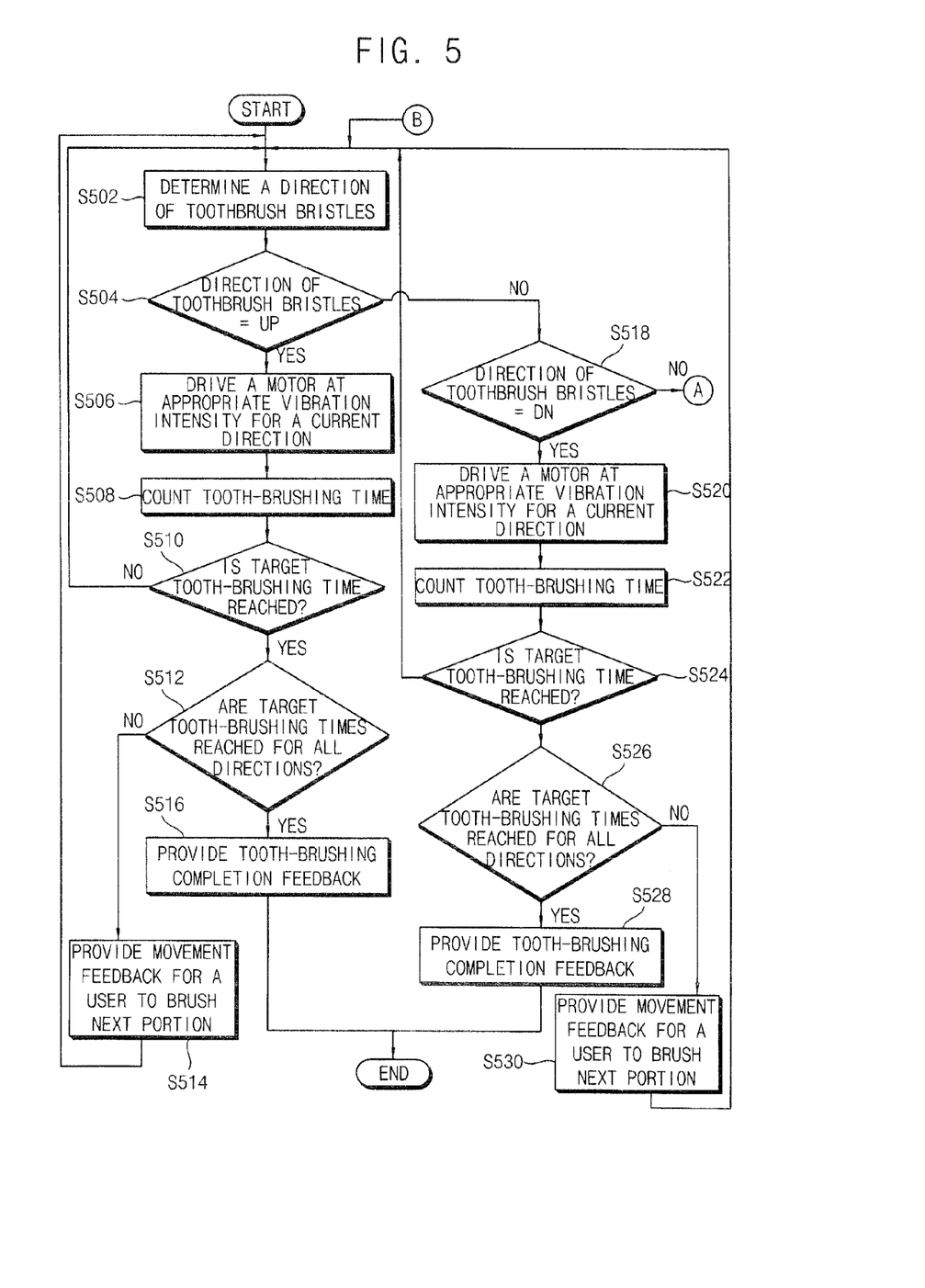
FIGS. 5 and 6 are a flowchart illustrating the entire operation of an electric toothbrush with a sensing function for the location of the toothbrush according to an example embodiment.
Figure 6:
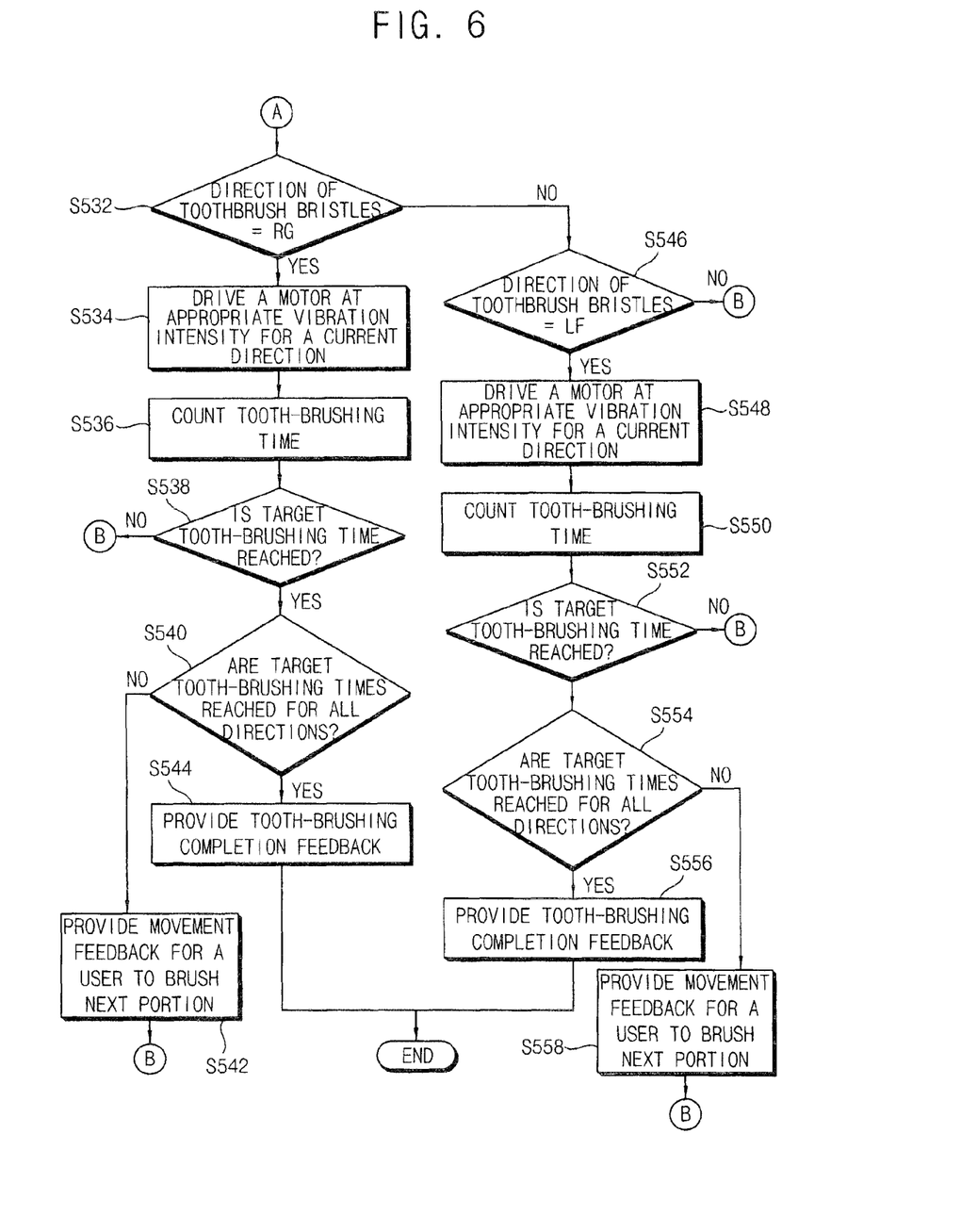

FIGS. 5 and 6 are a flowchart illustrating the entire operation of an electric toothbrush according to an example embodiment of the present invention;

If the electric toothbrush is initially powered on, a current direction of toothbrush bristles is determined among up, down, left and right directions (step S502, step S504, step S518, step S532 and step S546), and thus a vibration-generating unit, or a bristle-vibrating unit, is operated to vibrate the toothbrush bristles at predetermined vibration intensity according to the direction of toothbrush bristles (step S506, step S520, step S534 and step S548). Thereafter, toothbrushing time for a portion corresponding to the direction is counted (step S508, step S522, step S536 and step S550), and thus whether the toothbrushing time for the portion reaches a target toothbrushing time is determined (step S510, step S524, step S538 and step S552).

In a similar manner, whether the toothbrushing time for each of the other portions reaches a target toothbrushing time is determined (step S510, step S524, step S538 and step S552). If toothbrushing times for all the portions reach the target toothbrushing times (step S512: YES, step S526: YES, step S540: YES and step S554: YES), a toothbrushing completion feedback is provided for a user to finish the toothbrushing (step S516, step S528, step S544 and step S556). If the toothbrushing time for some portion does not reach the target toothbrushing time (step S512: NO, step S526: NO, step S540: NO and step S554: NO), a movement feedback indicating the user to brush the next portion is provided (step S514, step S530, step S542 and step S558).

In some embodiments, the target toothbrushing time for each portion of the teeth may be determined by dividing a total target toothbrushing time, for example 180 seconds, into four time periods, each of which has weight according to the number and sizes of teeth included in the corresponding portion. When the feedback in the steps described above are provided visually (e.g., by an LCD display or by a light-emitting diode (LED) arrow), auditorily (e.g., by a speaker, by a buzzer or by a piezoelectric material) or tactually (e.g., by vibration intensity or by a vibration pattern), and the feedback may be provided in real-time.

FIGS. 7 through 12 illustrate a bristle direction-sensing unit included in an electric toothbrush according to another example embodiment of the present invention.

Figure 7:
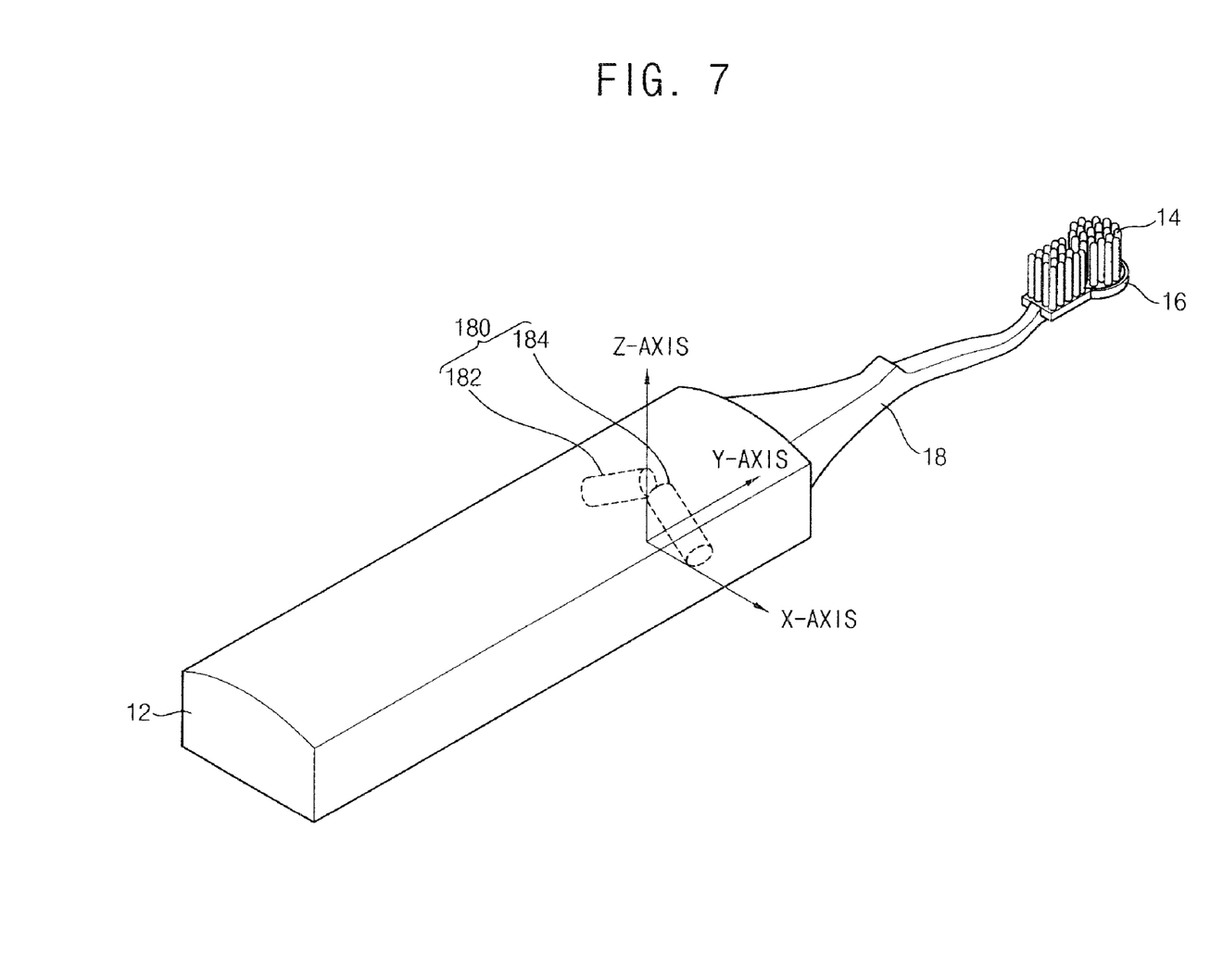
FIG. 7 is a schematic diagram illustrating an electric toothbrush including a bristle direction-sensing unit having inclination sensors according to an example embodiment.

Referring to FIG. 7, the bristle direction-sensing unit 180 of an inclination sensor type includes a pair of inclination sensors 182 and 184 installed in a toothbrush body 12. As illustrated in FIG. 7, the pair of inclination sensors 182 and 184 may be arranged in an x-axis direction, each of which faces the other sensor and is inclined at an angle θ with respect to the x-axis direction. When the electric toothbrush is positioned horizontally, an inclination sensor 182 is maintained in an ON state and the other inclination sensor 184 is maintained in an OFF state. Here, the angle θ may be in a range from about 15 degrees to about 35 degrees so that the inclination sensors 182 and 184 are maintained in a stable initial state, or in an ON state and in an OFF state, respectively, when the electric toothbrush is positioned horizontally. The inclination sensors 182 and 184 determine directions to which the toothbrush bristles 14 are directed among up, down, left and right directions by detecting an inclined state of the electric toothbrush.

Figure 8:
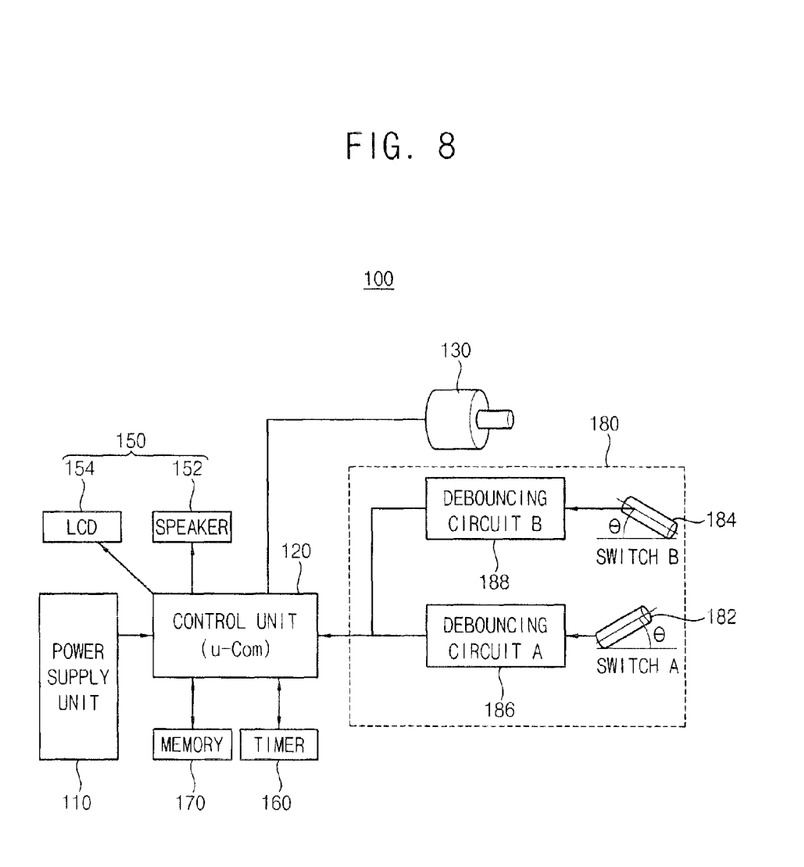
FIG. 8 is a block diagram illustrating an electrically powered unit included in the electric toothbrush of FIG. 7.

FIG. 8 is a block diagram illustrating an electrically powered unit included in the electric toothbrush of FIG. 7. Referring to FIG. 8, the electrically powered unit 100 of FIG. 8 has a similar configuration to the electrically powered unit 100 illustrated in FIG. 1, except for the bristle direction-sensing unit 180 of an inclination sensor type. Like numerals refer to like elements throughout.

The bristle direction-sensing unit 180 includes a first inclination sensor 182, a second inclination sensor 184, a first debouncing circuit 186 and a second debouncing circuit 188. The first debouncing circuit 186 reduces or removes bounce during a switching operation of the first inclination sensor 182 and the second debouncing circuit 188 reduces or removes bounce during a switching operation of the second inclination sensor 184 so as to provide a control unit 120 with a stable switching signal.

The control unit 120 may be programmed to determine directions to which toothbrush bristles are directed based on a combination of switched states of the inclination sensors 182 and 184 as described in Table 3.

TABLE 3

| FIRST INCLINATION SENSOR | SECOND INCLINATION SENSOR | BRISTLE DIRECTION |
| --- | --- | --- |
| ON | OFF | UP |
| ON | ON | RG (LEFT INCLINATION) |
| OFF | ON | DW |
| OFF | OFF | LF (RIGHT INCLINATION) |

FIGS. 9 through 12 illustrate switched states of the inclination sensors 182 and 184 for detecting four directions of up, down, left and right directions. Referring to FIGS. 9 through 12, each of the inclination sensors 182 and 184 includes a cover unit, a cup unit and a ball. If the ball is in contact with the cover unit, an inclination sensor is switched on since the cover unit is electrically coupled to the cup unit. If the ball is not in contact with the cover unit, the inclination sensor is switched off since the cover unit is electrically separated from the cup unit.

Figure 9:
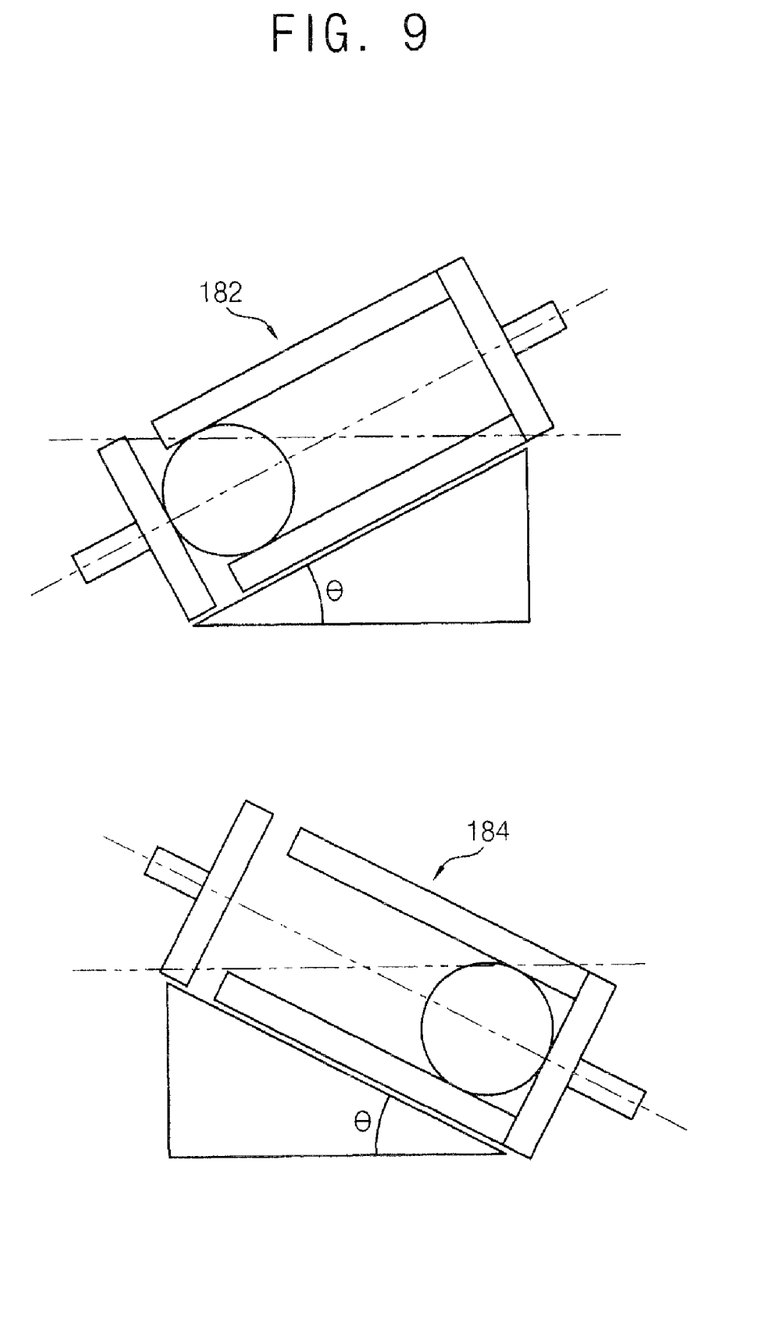
FIGS. 9 through 12 are diagrams for describing switching operations of inclination sensors.

If a direction of toothbrush bristles is an up direction UP (i.e., when the electric toothbrush is positioned horizontally), as illustrated in FIG. 9, the first inclination sensor 182 is maintained in an ON state and the second inclination sensor 184 is maintained in an OFF state, which indicates that the toothbrush bristles are in contact with the upper left and right occlusal sides.

Figure 10:
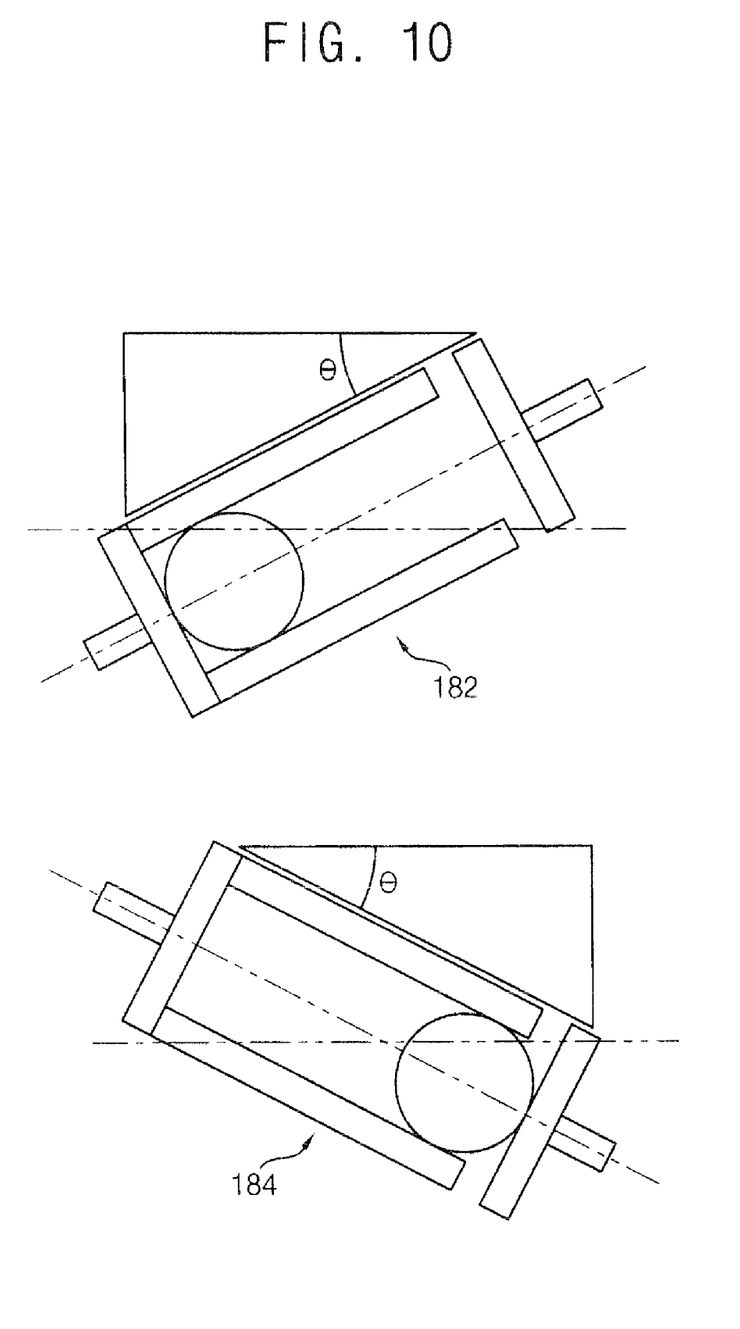

If the direction of toothbrush bristles is a down direction DW (i.e., when the electric toothbrush is turned upside down), as illustrated in FIG. 10, the first inclination sensor 182 is maintained in an OFF state and the second inclination sensor 184 is maintained in an ON state, which indicates that the toothbrush bristles are in contact with the lower left and right occlusal sides.

Figure 11:
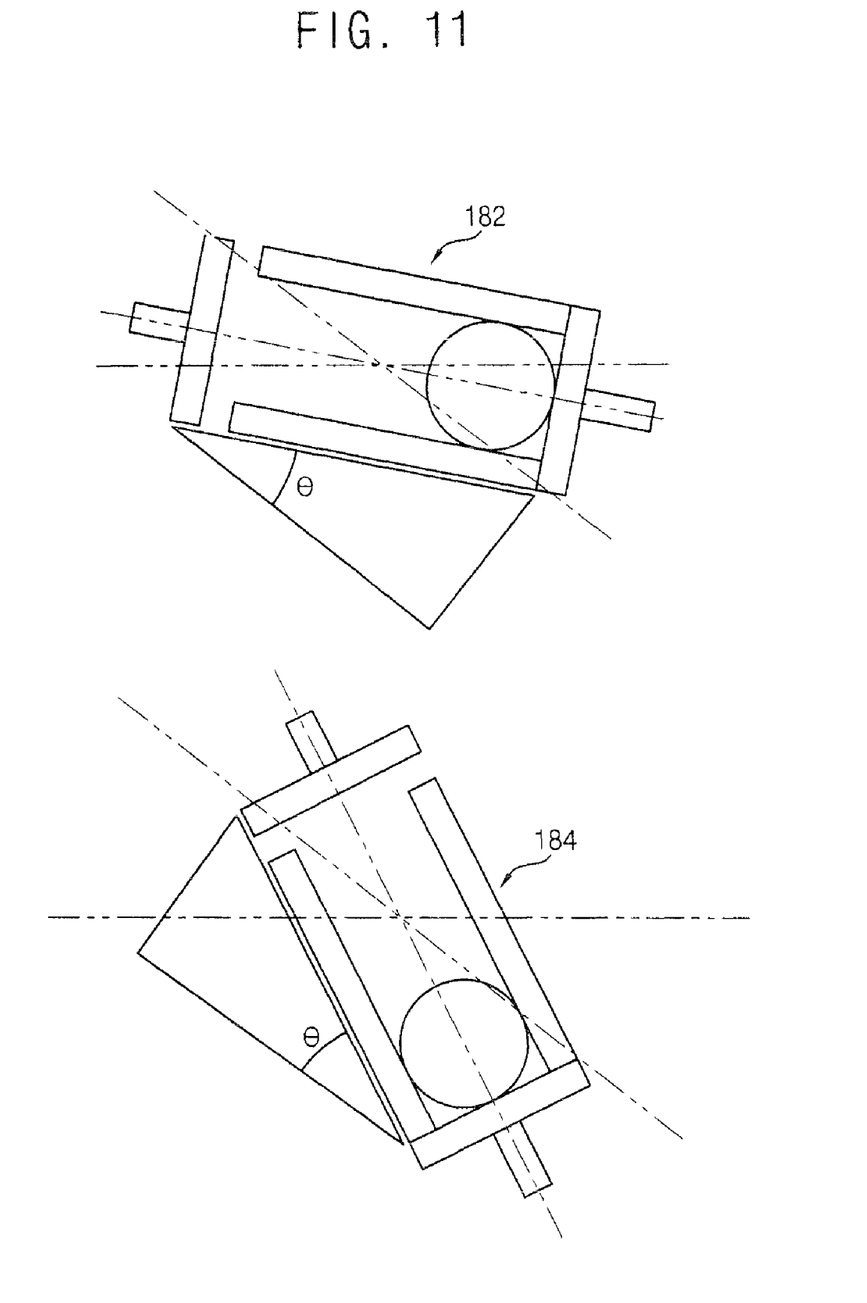

If the direction of the toothbrush bristles is a left direction LF (i.e., when the electric toothbrush is inclined right), as illustrated in FIG. 11, both the first inclination sensor 182 and the second inclination sensor 184 are maintained in an OFF state, which indicates that the toothbrush bristles are in contact with the buccal side of right molars or lingual side of left molars.

Figure 12:
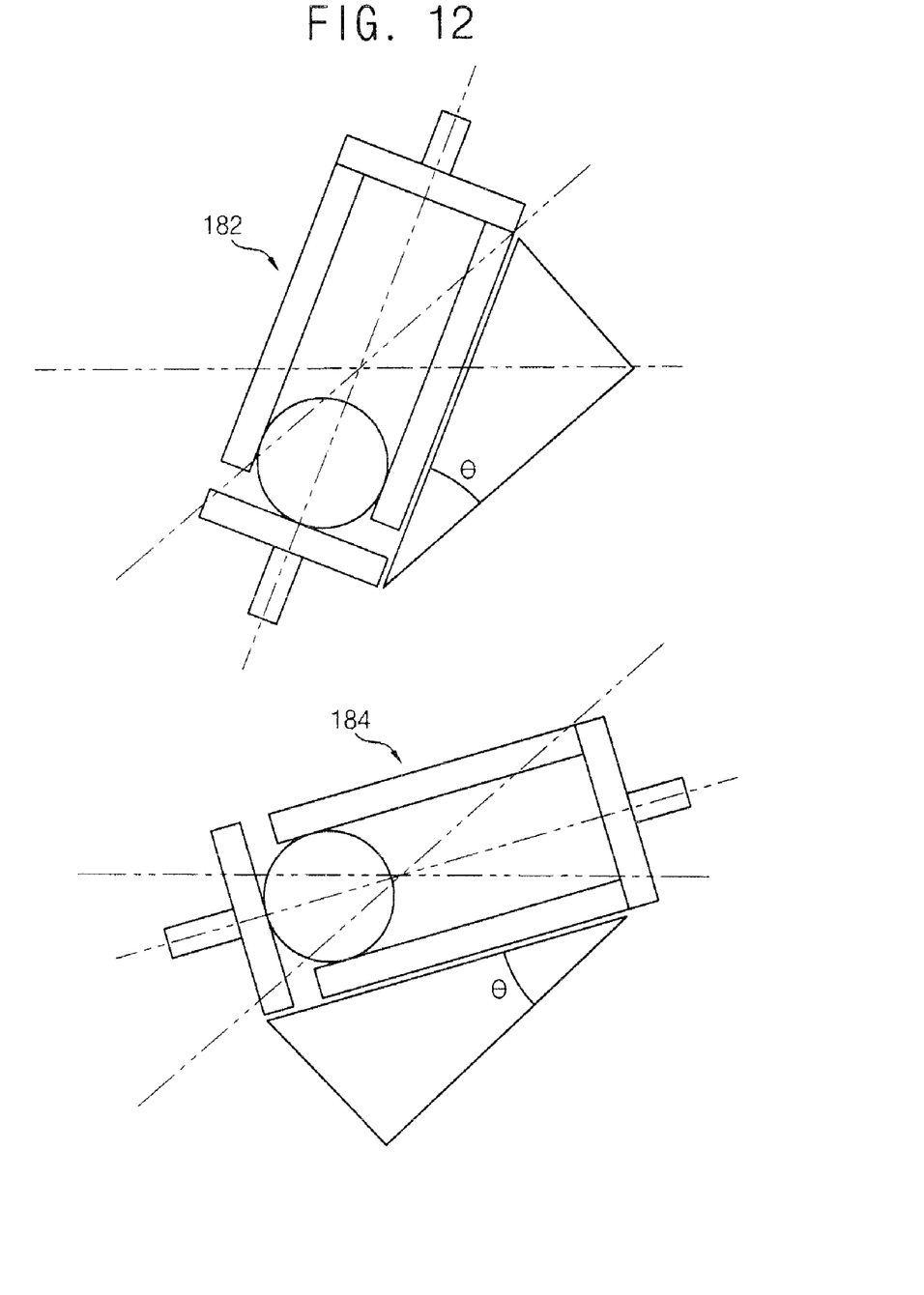

If the direction of toothbrush bristles is a right direction RF (i.e., when the electric toothbrush is inclined left), as illustrated in FIG. 12, both the first inclination sensor 182 and the second inclination sensor 184 are maintained in an ON state, which indicates that the toothbrush bristles are in contact with the buccal side of left molars, labial side of front teeth (if a user is right-handed) or lingual side of right molars.

Since the inclination sensor is cheaper than the acceleration sensor, the cost of an electric toothbrush may be reduced if the electric toothbrush employs the inclination sensor.

In the example embodiments described above, the inclination sensors are arranged in the x-axis direction. Alternatively, in some example embodiments, the inclination sensors may be arranged in the z-axis direction in order to detect the direction of the toothbrush bristles.

This invention has been described with reference to the example embodiments. It is evident, however, that many alternative modifications and variations will be apparent to those having skill in the art in light of the foregoing description. Accordingly, the present invention embraces all such alternative modifications and variations as fall within the spirit and scope of the appended claims.

INDUSTRIAL APPLICABILITY

As described above, the electric toothbrush according to some example embodiments may increase convenience of use by automatically controlling vibration intensity according to detected portions of teeth being brushed. Further, the electric toothbrush may provide motivation for a user to properly brush the teeth. The electric toothbrush may provide appropriate feedback for the user to uniformly brush the teeth so that the effect of toothbrushing may be increased.

The invention claimed is:

1. An electric toothbrush, comprising:
   a bristle-vibrating unit configured to vibrate toothbrush bristles to clean a side of teeth in contact with the toothbrush bristles;
   a bristle direction-sensing unit configured to detect a direction to which the toothbrush bristles are directed in an oral cavity, the direction being one of directions toward a buccal side, a lingual side and an occlusal side, the buccal side being an outer side of the teeth, the lingual side being an inner side of the teeth, and the occlusal side being a chewing side of the teeth; and
   a control unit configured to automatically control the bristle-vibrating unit in response to the detected direction such that the vibration intensity of the toothbrush bristles when the buccal side or the lingual side is brushed is weaker than the vibration intensity when the occlusal side is brushed.

2. The electric toothbrush of claim 1, wherein the bristle-vibrating unit includes a three-axis acceleration sensor, an x-axis of the three-axis acceleration sensor directed along a direction that is perpendicular to a toothbrush handle length direction and to a toothbrush bristle direction, a y-axis of the three-axis acceleration sensor directed along the toothbrush handle length direction, a z-axis of the three-axis acceleration sensor directed along the toothbrush bristle length direction.

3. The electric toothbrush of claim 1, wherein the bristle-vibrating unit includes a pair of acceleration sensors, axis directions of the acceleration sensors being perpendicular to a y-axis directed along a toothbrush handle length direction, the axis directions of the acceleration sensors being inclined at a positive predetermined angle and a negative predetermined angle, respectively, with reference to an x-axis that is perpendicular to the toothbrush handle length direction and to a toothbrush bristle direction, and the acceleration sensors arranged symmetrically to each other.

4. The electric toothbrush of claim 1, wherein the bristle direction-sensing unit detects the direction to which the toothbrush bristles are directed by dividing the detected direction into a direction toward an upper occlusal side, a direction toward a lower occlusal side, a direction toward a left buccal side or a left lingual side, and a direction toward a right buccal side or a right lingual side.

5. The electric toothbrush of claim 1, further comprising:
   a timer configured to count a toothbrushing time for the detected direction; and
   a feedback unit configured to provide a user with at least one of visual feedback, auditory feedback and tactile feedback when the counted toothbrushing time reaches a predetermined recommended toothbrushing time.

6. An electric toothbrush, comprising:
   a bristle-vibrating unit configured to vibrate toothbrush bristles to clean a side of teeth in contact with the toothbrush bristles;
   a bristle direction-sensing unit configured to detect a direction to which the toothbrush bristles are directed in an oral cavity, the direction being one of directions toward a buccal side, a lingual side and an occlusal side, the buccal side being an outer side of the teeth, the lingual side being an inner side of the teeth, and the occlusal side being a chewing side of the teeth;
   a timer configured to count a toothbrushing time for the detected direction;
   a feedback unit configured to provide a user with at least one of visual feedback, auditory feedback and tactile feedback, or any combination thereof; and
   a control unit configured to control the bristle-vibrating unit, and configured to control the feedback unit to provide the user with the at least one type of feedback when the counted toothbrushing time reaches a predetermined recommended toothbrushing time by checking the toothbrushing time provided from the timer in response to the detected direction,
   wherein the control unit configured to control a vibration intensity of the toothbrush bristles in response to the detected direction.

7. The electric toothbrush of claim 6, wherein the control unit is configured to control the feedback unit to provide the user with feedback about an insufficiency state if the toothbrushing time of any portion of the teeth is shorter than a predetermined recommended toothbrushing time by checking the toothbrushing time of each of a plurality of portions of the teeth in response to the detected direction.

8. An electric toothbrush, comprising:
   a bristle-vibrating unit configured to vibrate toothbrush bristles to clean a side of teeth in contact with the toothbrush bristles;
   a bristle direction-sensing unit configured to detect a direction to which the toothbrush bristles are directed in an oral cavity, and
   a control unit configured to control a vibration intensity of the toothbrush bristles in response to the detected direction.

9. An electric toothbrush system, comprising:
   a toothbrush body;
   a toothbrush head on which toothbrush bristles are formed;
   a toothbrush neck extending from the toothbrush head and is detachably attached to the toothbrush body;
   a vibrating unit configured to vibrate toothbrush bristles via the neck;
   a direction-sensing unit configured to detect an orientation of bristles;

a control unit configured to estimate a section of teeth being brushed based on the detected orientation of the bristles and to control a vibration intensity of the bristles based on the estimated section of the teeth; and a power supply unit to directly supply electronic power to at least one of the vibrating unit, the direction-sensing unit, and the control unit, wherein the vibrating unit, the direction-sensing unit, the control unit, and the power supply unit are embedded in the toothbrush body.

10. The electric toothbrush of claim 9, wherein the control unit configured to control the vibration intensity of the bristles in response to the detected direction.

11. The electric toothbrush of claim 9, wherein the direction-sensing unit includes at least of a pair of inclination sensors, the axis directions of the inclination sensors being perpendicular to the y-axis directed along the lengthwise direction of a toothbrush handle, and the axis directions of the inclination sensors being inclined at a positive predetermined angle and a negative predetermined angle, respectively, with reference to the x-axis that is perpendicular to the y-axis and to the lengthwise direction of the bristles, and the inclination sensors being arranged symmetrically to each other.

12. The electric toothbrush of claim 9, wherein the direction-sensing unit includes a three-axis acceleration sensor for detecting a three-dimensional orientation of the bristles based on output of the acceleration sensor.

13. The electric toothbrush of claim 9, wherein the direction-sensing unit detects a direction of the bristles by dividing the detected orientation into at least four directions.

14. The electric toothbrush of claim 13, wherein the four directions include a direction toward an upper occlusal side, a direction toward a lower occlusal side, a direction toward a left buccal side or a left lingual side, and a direction toward a right buccal side or a right lingual side.

15. The electric toothbrush of claim 14, wherein the control unit configured to automatically control the vibrating unit in response to the detected direction such that the vibration intensity of the bristles when the occlusal side is brushed is stronger than the vibration intensity when the buccal side or the lingual side is brushed.

16. The electric toothbrush of claim 9 further comprising:
a timer configured determine a duration of brushing time in a detected direction; and
a feedback unit configured to provide a user with at least one of visual feedback, auditory feedback, and tactile feedback to provide information to the user,
wherein the feedback unit and the timer are embedded in the toothbrush body.

17. The electric toothbrush of claim 16, wherein the visual feedback unit is a light-emitting diode (LED) display.

18. The electric toothbrush of claim 16, wherein the visual feedback unit is installed on an opposite side of the bristles.

19. The electric toothbrush of claim 16, wherein the visual feedback unit is installed on a back side of the toothbrush body.

20. The electric toothbrush of claim 16, further comprising:
a memory configured to store at least one of a start time of the brushing, duration of the brushing time in a detected direction, a score for the brushing, and total brushing time.

\* \* \* \* \*